(12) United States Patent
Rump et al.

(10) Patent No.: US 9,629,999 B2
(45) Date of Patent: Apr. 25, 2017

(54) IMPLANTABLE DEVICE WITH ELECTRICAL FILTER

(71) Applicant: BIOTRONIK SE & Co. KG, Berlin (DE)

(72) Inventors: Jens Rump, Berlin (DE); Michael Friedrich, Kleinmachnow (DE)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 14/793,836

(22) Filed: Jul. 8, 2015

(65) Prior Publication Data

US 2016/0045725 A1    Feb. 18, 2016

Related U.S. Application Data

(60) Provisional application No. 62/036,639, filed on Aug. 13, 2014.

(51) Int. Cl.
*A61N 1/05* (2006.01)
*A61N 1/08* (2006.01)
*H03J 1/06* (2006.01)

(52) U.S. Cl.
CPC .............. *A61N 1/08* (2013.01); *A61N 1/056* (2013.01); *H03J 1/06* (2013.01); *A61N 2001/086* (2013.01)

(58) Field of Classification Search
CPC .... A61N 1/08; A61N 1/056; A61N 2001/086; H03J 1/06
See application file for complete search history.

(56) References Cited

U.S. PATENT DOCUMENTS

| | | |
|---|---|---|
| 2009/0149906 A1 | 6/2009 | Ameri et al. |
| 2010/0099281 A1 | 4/2010 | Weiss et al. |
| 2011/0172756 A1 | 7/2011 | Doerr et al. |

OTHER PUBLICATIONS

European Search Report received from EP Application No. 15167595, dated Dec. 22, 2015, 5 pages.

*Primary Examiner* — Paula J Stice
(74) *Attorney, Agent, or Firm* — Arc IP Law, PC; Joseph J. Mayo

(57) ABSTRACT

An implantable device including a proximal end, a distal end, an elongate electrically conductive component arranged between the proximal end and the distal end, and a contact pole electrically connected to the elongate electrically conductive component. The contact pole is arranged in a region of the distal end to electrically contact bodily tissue adjacent to the contact pole during operation of the implantable device. The elongate electrically conductive component includes a sub-component connected in series with remaining portions of the elongate electrically conductive component. The sub-component includes a capacitive component, an inductive component and a magneto-resistive component, which are arranged to cause a reduction of a resistivity of the magneto-resistive component that leads to a shift of a resonance frequency of the sub-component.

15 Claims, 10 Drawing Sheets

IMPLANTABLE DEVICE WITH ELECTRICAL FILTER

This application claims the benefit of U.S. Provisional Patent Application 62/036,639 filed on 13 Aug. 2014, the specification of which is hereby incorporated herein by reference.

BACKGROUND OF THE INVENTION

Field of the Invention

Embodiments of the invention generally relate to a permanently or temporarily implantable device including a proximal end, a distal end, an elongate electrically conductive component arranged therebetween, and a contact pole. In embodiments of the invention, the contact pole is arranged in a region of the distal end of the device to electrically contact bodily tissue adjacent to the contact pole during operation of the implantable device, wherein the contact pole is electrically connected to the elongate electrically conductive component.

Description of the Related Art

Generally, implantable devices, for example electrode lines for electrostimulation, have the disadvantage that their electrical conductor, such as an elongate electrically conductive component, may heat up in an MRI scanner due to the alternating magnetic fields prevailing in the MRI scanner that induce electrical currents in the electrical conductor that are not insignificant. Therefore, cardiac pacemaker patients nowadays cannot generally be examined in an MRI scanner or may only be examined to a limited extent.

Specifically, at least one stimulation electrode line is typically connected to implantable cardiac pacemakers or defibrillators, and, at its proximal end, intended for connection to the cardiac pacemaker or defibrillator. The electrode line includes a standardized electrical terminal, and, at its distal end, intended for placement in the heart, the electrode line includes one or more electrode poles as contact poles for contacting bodily tissue. Such a contact pole, generally, is used to deliver electrical pulses to the tissue (myocardium) of the heart or to sense electrical fields in order to sense cardiac activity, generally known as sensing. For this purpose, contact poles typically form electrically conductive surface portions of an electrode line. Contact poles are typically provided as ring electrodes in the form of a ring around the electrode line or in the form of a point electrode or tip electrode at the distal end of the electrode line. The contact poles are generally electrically conductively connected via one or more electrical conductors to terminal contacts of the electrical terminal of the electrode line at the proximal end thereof. The respective electrical conductors typically form elongate electrically conductive components of the electrode line as an implantable device. One or more electrical conductors, which generally electrically connect one or more of the electrode poles to one or more of the contacts, typically run between the terminal contacts of the electrical terminal of the electrode lines at the proximal ends thereof and the electrode poles at the distal end of the electrode line. These electrical conductors, generally, may be used on one hand for transmission of stimulation pulses to the electrode poles and on the other hand for transmission of electrical signals, received by the electrode poles, to the proximal end of the electrode line, referred to herein as a function line. Such function lines, typically, are electrical conductors necessary for the functions of the respective electrode line and as such are exposed to the risk that electrical currents are induced therein as a result of external alternating magnetic fields. Generally, the currents, for example, may lead to an undesirable heating of the function lines or of the electrode poles connected thereto, or may lead to the delivery of corresponding currents via the electrode poles to surrounding tissue, and therefore to a heating of the surrounding tissue. In addition, there is the risk that the external fields lead to signal-falsifying interferences.

BRIEF SUMMARY OF THE INVENTION

One or more embodiments of the invention provide a device that may be used in a magnetic resonance imaging scanner.

At least one embodiment of the invention includes a device with an elongate electrically conductive component that includes a sub-component. In one or more embodiments, the sub-component is connected in series with the rest, or a remainder, of the elongate electrically conductive component. In at least one embodiment, the sub-component includes at least one capacitive component, at least one inductive component and at least one magneto-resistive component, arranged such that a reduction of a resistivity of the at least one magneto-resistive component leads to a shift of a resonance frequency of the sub-component.

Inductances and capacitances, in at least one embodiment of the invention, for example parasitic capacitances, may be connected in parallel to the sub-component that is connected in series with the rest of the elongate electrically conductive component. In one or more embodiments, the sub-component connected in series may include high impedances (>1 kOhm) with electric waves in the radio frequency range. In at least one embodiment, the sub-component connected in series may act as a filter element. In one or more embodiments, the at least one magneto-resistive component may include a property of having a lower resistance in the presence of a magnetic field and may therefore change the capacitive and/or the inductive component of the sub-component connected in series. For example, in at least one embodiment, the at least one magneto-resistive component may change the capacitive and/or the inductive component by a short circuit, such that the inductance and/or the capacitance over a portion of the filter element may be significantly reduced in the presence of magnetic fields, as a result of the short circuit. In at least one embodiment, with the modified inductance, the resonance frequency of the filter element changes, and the filter element may be adjusted to the Larmor frequency of various magnetic resonance imaging scanners as a result of the magnetic field.

In at least one embodiment of the invention, an electric part may be provided that includes a plurality of components, wherein the plurality of components include at least one inductive component, at least one capacitive component and at least one magneto-resistive component. In one or more embodiments, the plurality of components may be arranged and interconnected such that the electric part includes different frequency responses depending on whether the electric part is exposed to a magnetic field.

By way of at least one embodiment, the magneto-resistive component may include a material of which the electrical resistance decreases under the influence of a magnetic field. In one or more embodiments, the magneto-resistive component may be arranged such that it at least partially bridges a gap or slit between electrically conductive elements or a gap or slit in an electrically conductive element of the sub-component connected in series.

According to at least one embodiment, the magneto-resistive component may include a material having at least one of the following properties: a giant magnetoresistance (GMR) effect, an anisotropic magnetoresistance (AMR) effect, a colossal magnetoresistance (CMR) effect and a tunnel magnetoresistance (TMR) effect.

In one or more embodiments, the magneto-resistive component may include alternating layers of ferromagnetic and non-magnetic material. In at least one embodiment, the magneto-resistive component may be printed onto a substrate.

By way of one or more embodiments, the inductive component may include a wire wound in a coiled manner onto a slitted metal sleeve and/or a metalized film wound in a spiraled manner onto a slitted metal sleeve.

In at least one embodiment, the capacitive component may include a slitted double sleeve.

In one or more embodiments, the capacitive, the inductive and the magneto-resistive component of the sub-component connected in series may be arranged and connected such that a reduction of the resistivity of the magneto-resistive component leads to a reduced inductance of the inductive component.

By way of at least one embodiment, the capacitive, the inductive and the magneto-resistive component of the sub-component connected in series may be arranged and connected such that a reduction of the resistivity of the magneto-resistive component leads to a reduced capacitance of the capacitive component.

In one or more embodiments, the capacitive, the inductive and the magneto-resistive component of the sub-component connected in series may be arranged and connected such that a reduction of the resistivity of the magneto-resistive component leads both to a reduced capacitance of the capacitive component and to a reduced inductance of the inductive component.

In at least one embodiment of the invention, the capacitive, the inductive and the magneto-resistive component of the sub-component connected in series may be arranged and connected such that a reduction of the resistivity of the magneto-resistive component leads to at least a partial short circuit of the inductive component and therefore to a change of the inductance.

In one or more embodiments, the capacitive, the inductive and the magneto-resistive component of the sub-component connected in series may be arranged and connected in such a way that a reduction of the resistivity of the magneto-resistive component leads to at least a partial short circuit of the capacitive component and therefore to a change of the capacitance.

In at least one embodiment, the capacitive, the inductive and the magneto-resistive component of the sub-component connected in series may be arranged and connected such that a reduction of the resistivity of the magneto-resistive component leads to a further inductance, which counteracts the inductance of the inductive component.

In one or more embodiments of the invention, the capacitive, the inductive and the magneto-resistive component of the sub-component connected in series may be arranged and connected such that a reduction of the resistivity of the magneto-resistive component leads to a transformation of the inductance of the inductive component toward a reduced inductance.

Other embodiments of the invention may include some or all of the features disclosed herein.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1A:
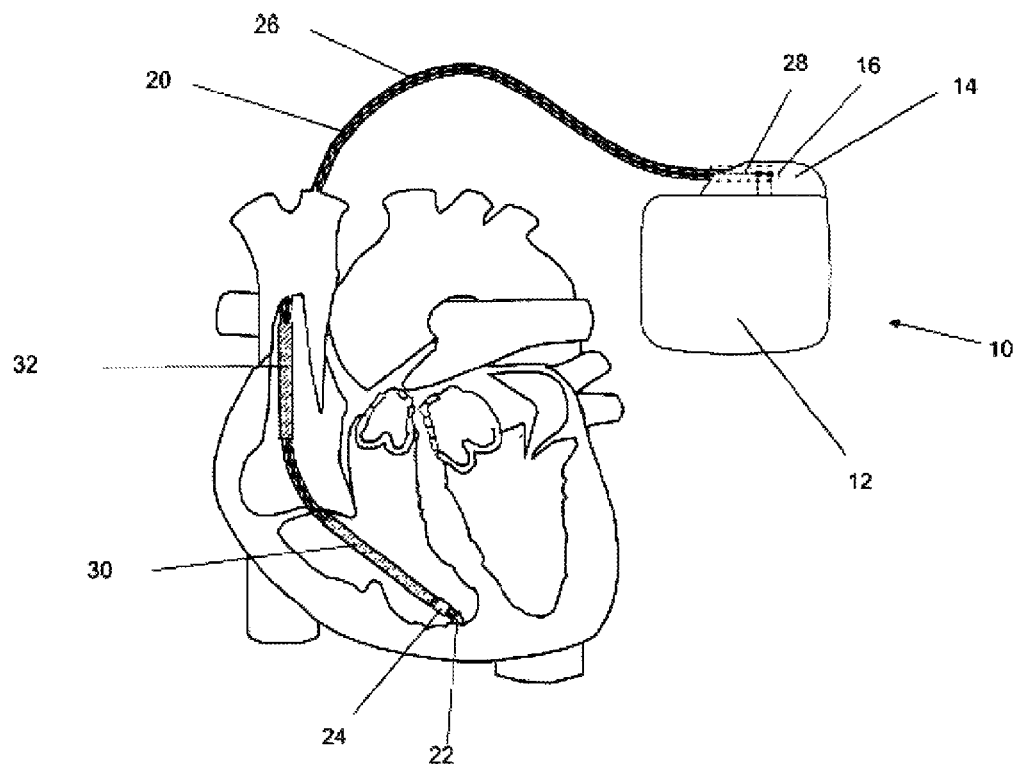
FIG. 1 shows an implantable heart stimulator and an implantable electrode line connected thereto.
Figure 1B:
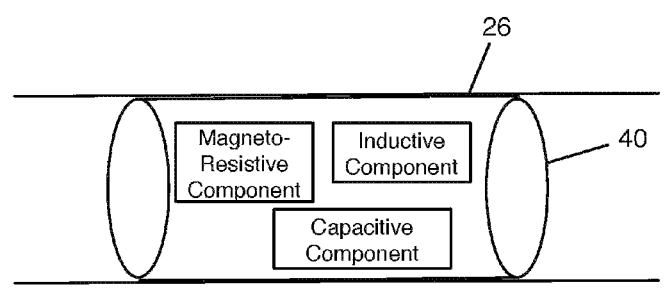

FIG. 1 shows, as implantable medical devices, an implantable heart stimulator 10 and an implantable electrode line 20 connected thereto, according to one or more embodiments of the invention.

In one or more embodiments, the implantable heart stimulator 10 may be a cardiac pacemaker or a cardioverter/defibrillator (ICD). In at least one embodiment, the heart stimulator 10 may be a ventricular pacemaker and defibrillator. Other heart stimulators, in at least one embodiment, may include dual-chamber cardiac pacemakers to stimulate the right atrium and the right ventricle, or biventricular cardiac pacemakers, which may also stimulate the left ventricle in addition to the right ventricle.

In one or more embodiments, the stimulator may include a housing 12, which may include metal that is electrically conductive and may serve as a large-area electrode pole. In at least one embodiment, a terminal housing 14 may be fastened to the outer face of the housing 12, also referred to as a header. In one or more embodiments, the header may include contact sockets that receive plug contacts. The contact sockets, in at least one embodiment, may include electrical contacts 16 connected via corresponding conductors to an electronics unit arranged in the housing 12 of the heart stimulator 10.

According to one or more embodiments of the invention, the electrode line 20 may be or include an implantable medical device. At least one embodiment of the invention may include electrode poles in the form of a point or tip electrode 22 and a ring electrode 24 arranged at a distal end of the electrode line 20. In at least one embodiment, the electrode poles 22 and 24 may be used, depending on the function of a heart stimulator to which the electrode line 20 is connected, to sense electrical potentials of the heart tissue (myocardium) or to deliver electrical signals, for example to deliver stimulation pulses, to the surrounding heart tissue. By way of one or more embodiments, FIG. 1 shows the electrode poles, such as the tip electrode 22 and the ring electrode 24, in the event of use of the electrode line 20, located in the apex of the right ventricle of a heart.

In at least one embodiment, both the tip electrode 22 and the ring electrode 24 may be electrically connected in each case via at least one electrical conductor 26 to a plug contact 28 at a proximal end of the electrode line 20. In one or more embodiments, the plug contact 28 may include electrical contacts that correspond to the electrical contacts 16 of the contact socket in the terminal housing 14 of the implantable heart stimulator 10. In at least one embodiment, the electrical conductors 26 in the electrode line 20 may be formed as approximately elongate cable conductors or as helically coiled conductors. Such conductors, according to one or more embodiments, which electrically conductively connect the function electrode poles to electrical contacts of the plug contact at the proximal end of the electrode line 20, are referred to herein within the scope of the invention as function conductors. In at least one embodiment, for example, the conductors or function conductors may transmit electrical signals used in therapy from the plug contact to the respective electrode pole or may guide sensed signals representing electrical potentials from the respective electrode pole to the plug contact and are therefore used during the basic function of the medical device.

In one or more embodiments, the electrical conductors 26, which connect the electrode poles 22 and 24 to the electrical contacts of the plug 28 of the electrode line 20, may be surrounded over the majority of their length by an insulating sleeve, such that electrical contact of the tissue of the heart is produced selectively via the electrode poles.

According to at least one embodiment, alternatively to or in addition to the electrode poles 22 and 24 used to stimulate the heart tissue, such as ventricular stimulation, the electrode line 20 may include two electrode poles 30 and 32. In one or more embodiments, the electrode poles 30 and 32 may have a greater area, may be used as defibrillation electrodes, and may be formed by at least one bare helically wound wire.

It is noted wherein one or more embodiments of the invention explained herein are within the scope of a right-ventricular cardiac pacemaker and defibrillator. However, within the context of the invention, one or more embodiments may include an ablation electrode line as a medical device, for example, wherein the ablation electrode line may protrude into the heart of a patient, be controlled by a device arranged outside the patient and be connected thereto.

In at least one embodiment, as shown in FIG. 1, the electrode line 20 forms the implantable device with its proximal and its distal end. In one or more embodiments, the conductor 26 of the electrode line 20 may form an elongate electrically conductive component arranged between the proximal and the distal end of the electrode line 20. In at least one embodiment, the electrode poles 22 and 24 may each form a contact pole, which is arranged in the region of the distal end of the electrode line 20, to electrically contact bodily tissue adjacent to the contact pole during operation. In one or more embodiments, the contact pole may be electrically connected to the elongate electrically conductive component, such as the conductor 26.

FIGS. 2 to 9 each show one or more embodiments of the invention of a sub-component 40 of the electrode line 20, wherein the sub-component 40 is connected in series to the conductor 26 of the electrode line 20.

In at least one embodiment, the conductor 26 may be formed at least in portions by a wire coil 42, which has a proximal portion 42A and a distal portion 42B, between which the sub-component 40 is arranged.

Figure 2:
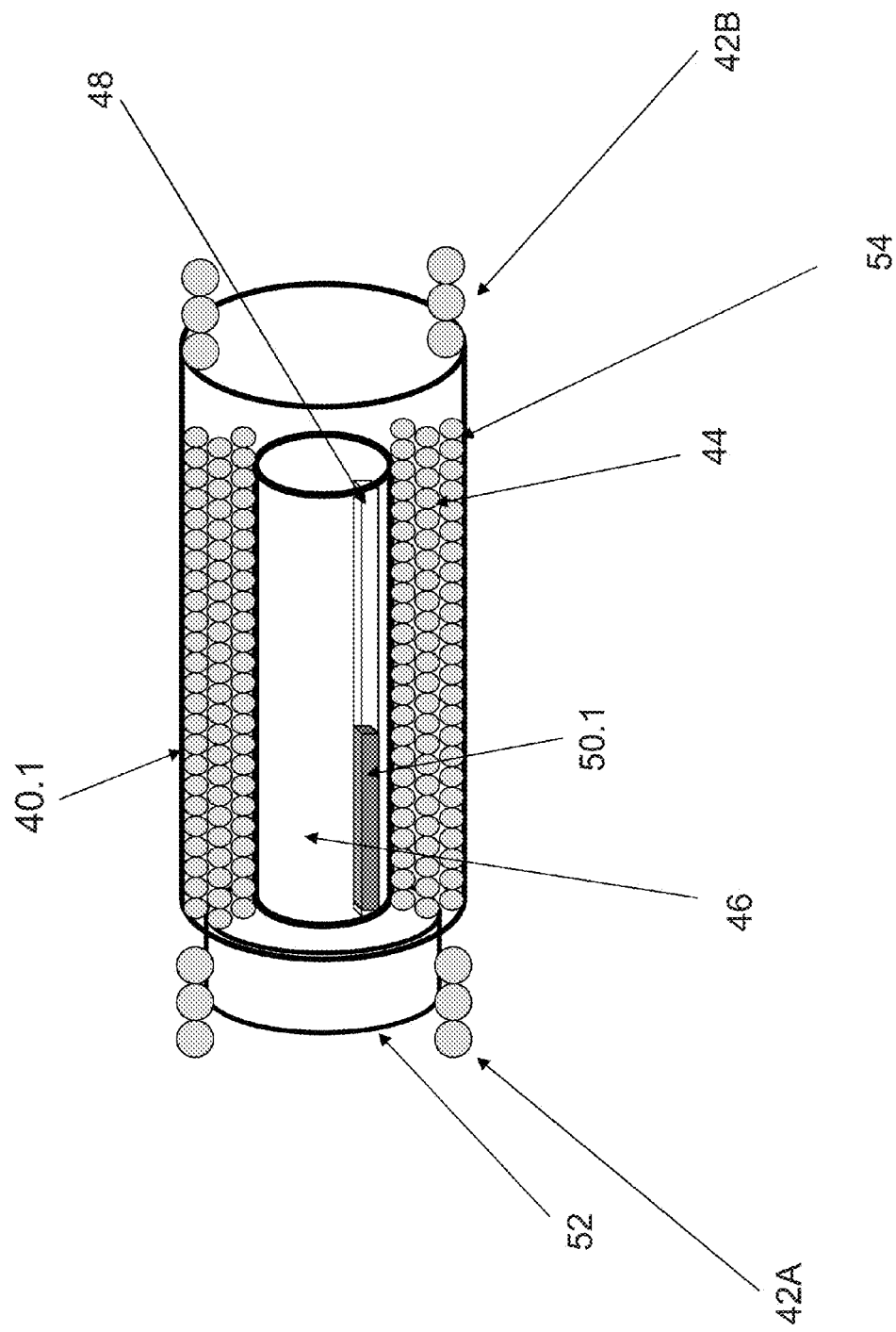
FIG. 2 shows a first embodiment of a sub-component according to the invention of an implantable device.

In at least one embodiment of the invention, with the sub-component 40.1 as shown in FIG. 2, the sub-component 40.1 may include a wire 44 wound in a coiled manner as an inductive component. In one or more embodiments, the capacitive component may be produced from the parasitic capacitances between the wire windings of the wire 44 wound in a coiled manner.

In at least one embodiment, the wire 44 may be wound on a longitudinally slitted electrically conductive metal sleeve 46.

By way of one or more embodiments, a longitudinal slit 48 in the metal sleeve 46 may be filled at least in part with magneto-resistive material 50.1, which forms the magneto-resistive component and bridges the slit 48 at least over a partial length. In at least one embodiment, the magneto-resistive component 50.1 may include the property of having a low electrical resistance in the presence of a magnetic field. As such, in at least one embodiment, the two edges of the metal sleeve 46, which are opposite one another in the region of the slit 48 and between which the magneto-resistive material 50.1 is arranged, may be electrically interconnected, for example short-circuited, via the magneto-resistive material 50.1. If there is no external magnetic field present, according to at least one embodiment, the magneto-resistive material 50.1 is highly resistive and a current flow beyond the slit 48 is prevented or at least severely limited.

According to one or more embodiments, if the magneto-resistive material 50.1 is low-resistance, the slitted metal sleeve 46 acts as a non-slitted, closed metal sleeve, at least where the slit 48 is bridged by the magneto-resistive material 50.1, and thus acts as a short-circuited coil with a single loop. As such, in at least one embodiment, the inductance of the windings of the outer coil, which is formed by the wound wire 44 and which are arranged above the short-circuited metal sleeve, may be transformed by the short circuited metal sleeve such that the resultant inductance is close to or equal to 0 henrys. In one or more embodiments, the magneto-resistive material 50.1 includes a low electrical resistance under the influence of an external magnetic field. In at least one embodiment, the inductance of the sub-component 40.1 may then break down over the metal sleeve 46 short-circuited by the magneto-resistive material 50.1. In one or more embodiments, the total inductance of the sub-component 40.1 may thus decrease sharply and the resonance frequency of the sub-component 40.1 increases accordingly.

In order to electrically connect the sub-component 40.1 to the wire coil 42, at least one embodiment of the invention may include an electrically conductive stop sleeve 52, connected to an outer sleeve 54, which is electrically conductive. In one or more embodiments, the outer coil formed by the wound wire 44 and also the slitted metal sleeve 46 and magneto-resistive material 50.1 may be arranged within the outer sleeve 54. In at least one embodiment, the distal portion 42B of the wire coil 42 may be electrically connected to the outer sleeve 54.

Figure 3:
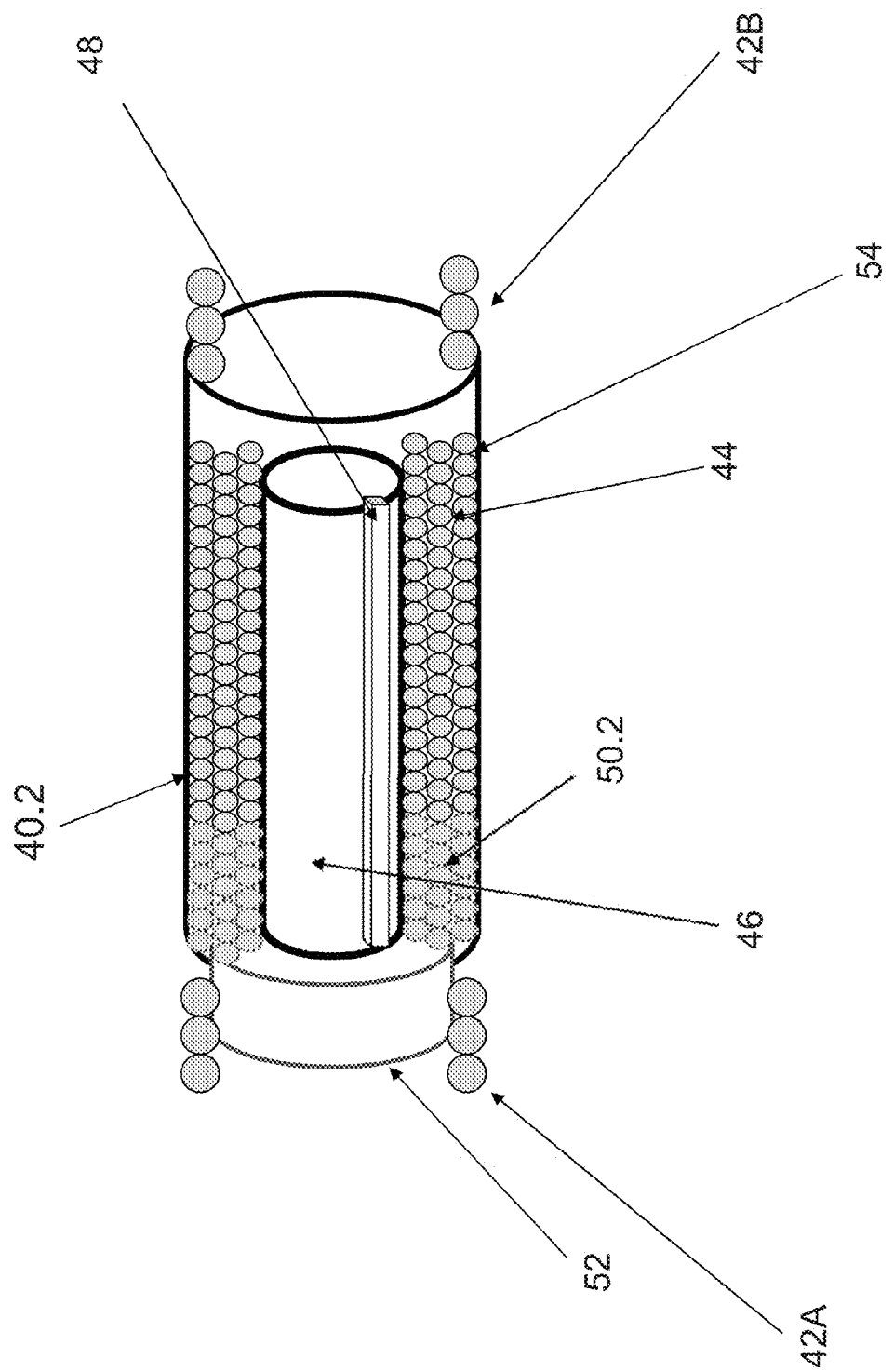
FIG. 3 shows a second embodiment of a sub-component according to the invention of an implantable device.

According to one or more embodiments, the structure of the sub-component 40.2 shown in FIG. 3 is similar in many respects to the structure of the sub-component 40.1 shown in FIG. 2. In particular, in at least one embodiment, a proximal portion 42A and a distal portion 42B of the wire coil 42 serving as conductor 26, the stop sleeve 52 and the outer sleeve 54 are shown in FIG. 3. In one or more embodiments, the inductive, the capacitive and the magneto-resistive component of the sub-component 40.2 may be arranged within the outer sleeve 54.

In at least one embodiment of the invention, the inductive component of the sub-component 40.2 may be formed by a wire 44, such as wound in a coiled manner and wound around a slitted inner sleeve 46. As such, in at least one embodiment, the inner sleeve 46 may include metal, but may not be a metal sleeve. If the inner sleeve 46 is not a metal sleeve, in at least one embodiment, but consists of non-conductive material, it may not require a slit 48.

According to one or more embodiments, the capacitive component of the sub-component 40.2 may be produced from the parasitic capacitances between the wire windings of the wire 44 wound in a coiled manner.

In contrast to the embodiment shown in FIG. 2, part of the wire shown in FIG. 3, by way of at least one embodiment, may be coated with magneto-resistive material 50.2. For example, in one or more embodiments, the magneto-resistive material 50.2, which forms the magneto-resistive component, may be located between individual windings of the wire 44 wound in a coiled manner, and may short-circuit the windings with one another or insulate them from one another, depending on whether the magneto-resistive material 50.2 includes a low or high electrical resistance. By way of at least one embodiment, if the magneto-resistive material 50.2 includes a low electrical resistance in the presence of a magnetic field, the coil portion in which the windings of the wire 44 are coated with the magneto-resistive material 50.2 is short-circuited, such that the coil portion may no longer contribute to the total inductance of the sub-component 40.2. In one or more embodiments, if there is no external magnetic field present, such that the magneto-resistive component 50.2 includes a high electrical resistance, the total inductance of the sub-component 40.2 may be higher accordingly.

As also shown in FIG. 3, in one or more embodiments, the resonance frequency of the sub-component 40.2 may increase in the presence of a magnetic field as a result of the then lower total inductance.

Figure 4:
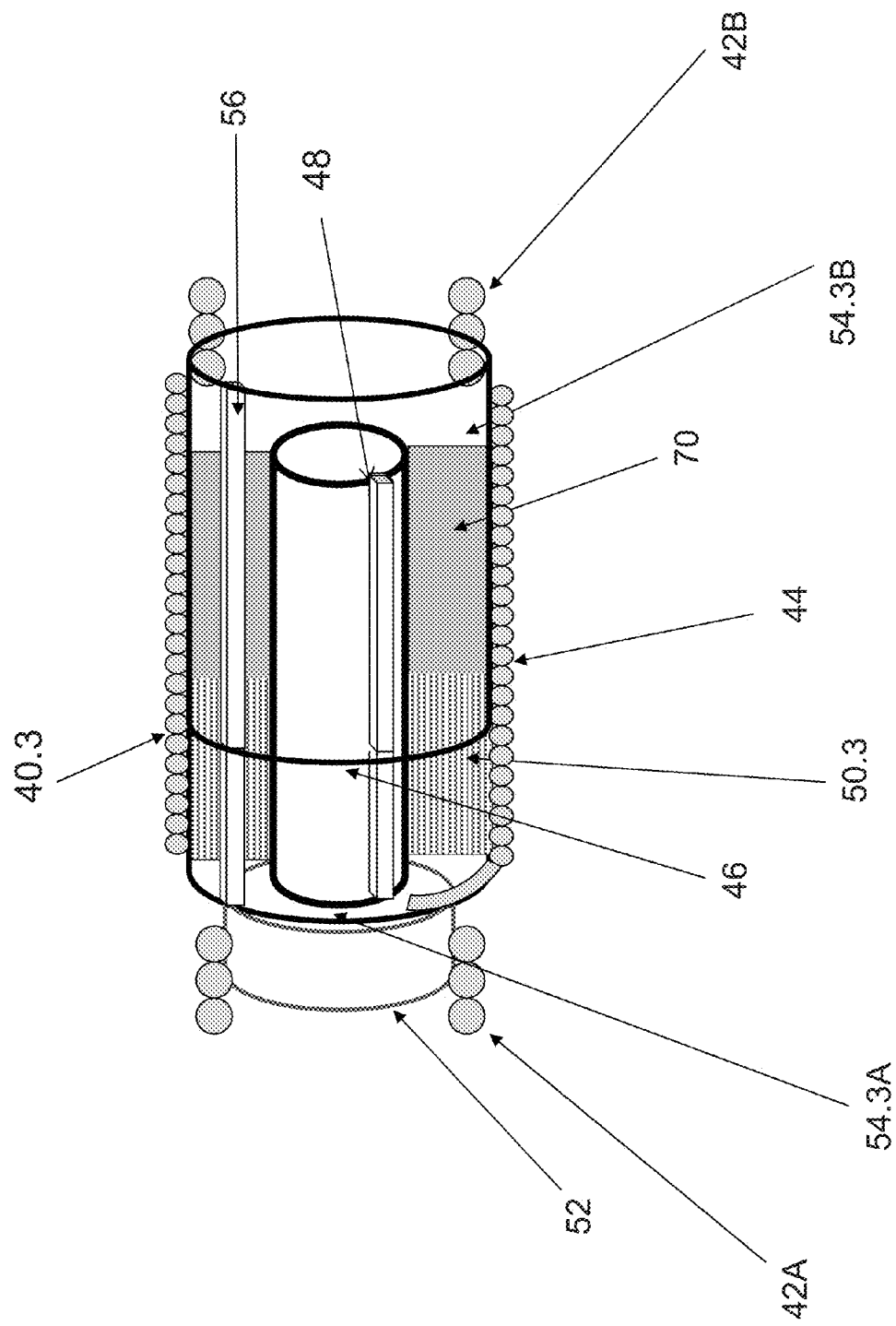
FIG. 4 shows a third embodiment of a sub-component according to the invention of an implantable device.

As shown in FIG. 4, the sub-component 40.3 may include a stop sleeve 52 and an outer sleeve 54, as also shown in FIG. 2 and FIG. 3, which electrically contact the proximal portion 42A and the distal portion 42B of the wire coil 42 respectively.

In at least one embodiment of the invention, as shown in FIG. 4, the outer sleeve 54.3 of the sub-component 40.3 may be slitted and may include a slit 56. In one or more embodiments, the outer sleeve 54.3 may be a longitudinally slitted, electrically conductive, double metal sleeve. In at least one embodiment, the inductive component of the sub-component 40.3 may be produced from a wire 44, which is wound in a coiled manner and which may be wound on the longitudinally slitted, electrically conductive double metal sleeve 54.3.

In one or more embodiments of the invention, the capacitive component of the sub-component 40.3 may be formed by the electrically conductive double metal sleeve 54.3, in which a dielectric 70 is arranged in the distal portion 54.3B of the double metal sleeve between the inner sleeve part 46 and the outer sleeve part. As such, in at least one embodiment, the inner and outer sleeve part of the double metal sleeve 54.3 may act capacitively. In order to retain a high capacitance, according to one or more embodiments, the distance between the inner and outer part of the double metal sleeve 54.3 is low. In at least one embodiment, a magneto-resistive material 50.3 may be provided in the proximal portion 54.3A between the inner and the outer part of the double metal sleeve 54.3.

In at least one embodiment, a capacitive component of the sub-component 40.3 may be provided by the parasitic capacitances between the wire windings of the wire 44 wound in a coiled manner, such that the total capacitance of the sub-component 40.3 is produced from the parasitic components between the wire windings and the capacitances between the inner and outer parts of the double metal sleeve 54.3.

Provided there is no sufficiently strong external magnetic field present, by way of one or more embodiments, the magneto-resistive material 50.3 between the inner and outer part of the proximal portion 54.3A of the double metal sleeve 54.3 may include a high electrical resistance and may act as a dielectric.

If a sufficiently strong external magnetic field is present, by way of one or more embodiments, the magneto-resistive material 50.3 may include a low electrical resistance and the capacitance of the proximal portion 54.3A of the double metal sleeve 54.3 decreases. At the same time, in at least one embodiment, the inductance of the sub-component 40.3 may also decrease, since the longitudinally slitted, electrically conductive double metal sleeve may also be short-circuited in its proximal portion 54.3A beyond the slit and thus acts as a short-circuited coil. Therefore, in one or more embodiments, the inductance of the sub-component 40.3 may also decrease, as described above according to FIG. 2.

Figure 5:
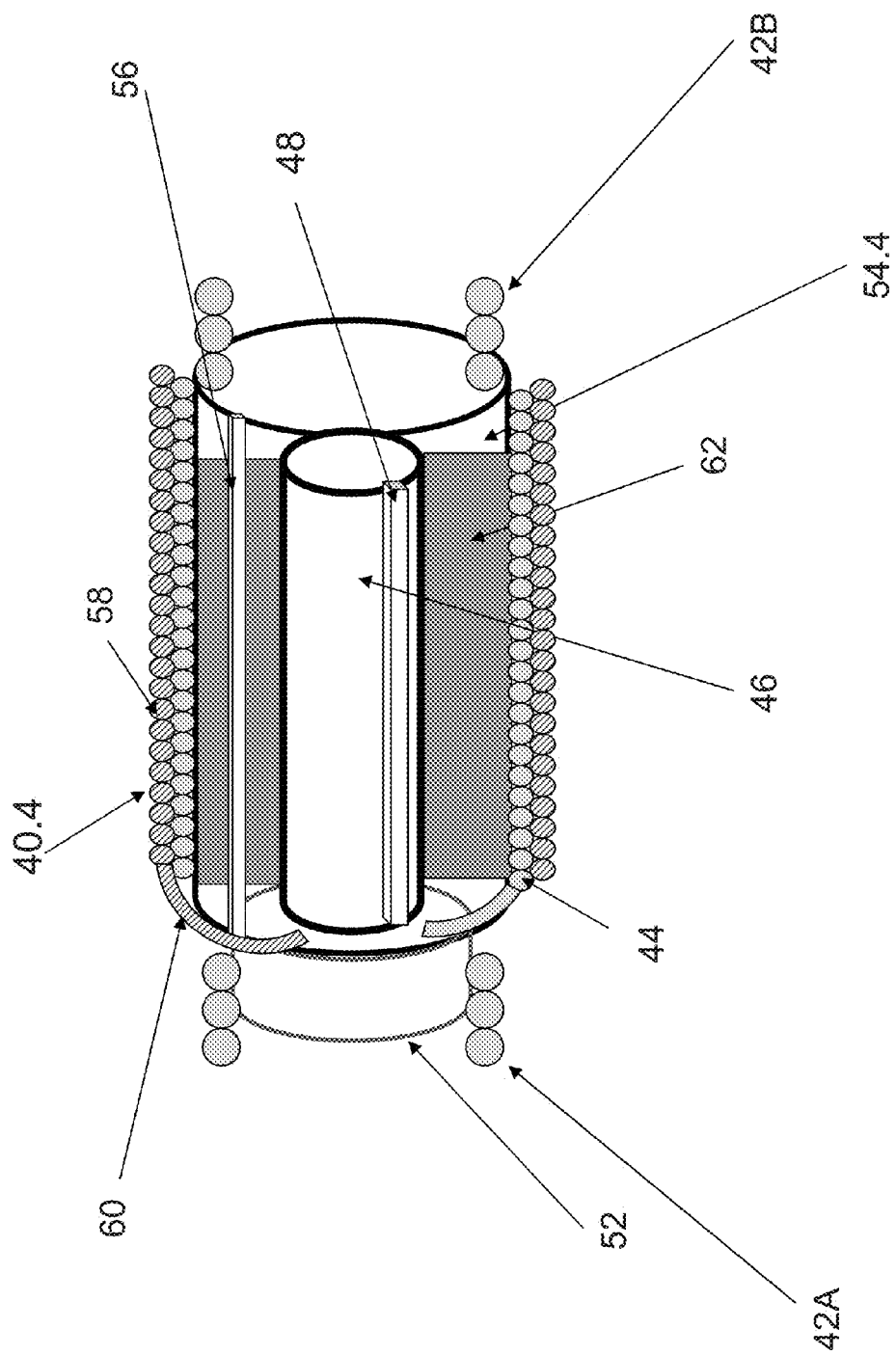
FIG. 5 shows a fourth embodiment of a sub-component according to the invention of an implantable device.
Figure 6:
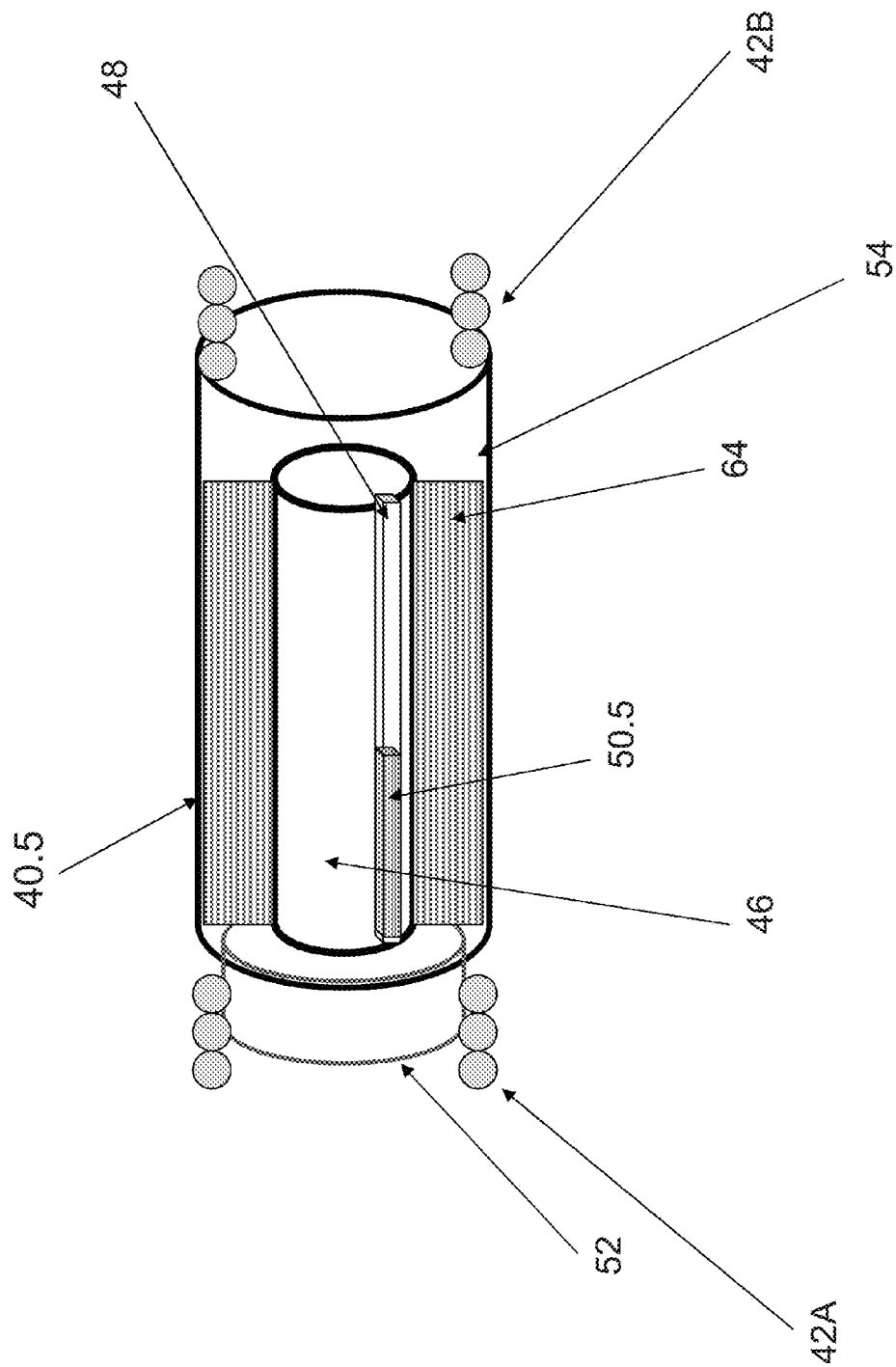
FIG. 6 shows a fifth embodiment of a sub-component according to the invention of an implantable device.
Figure 7:
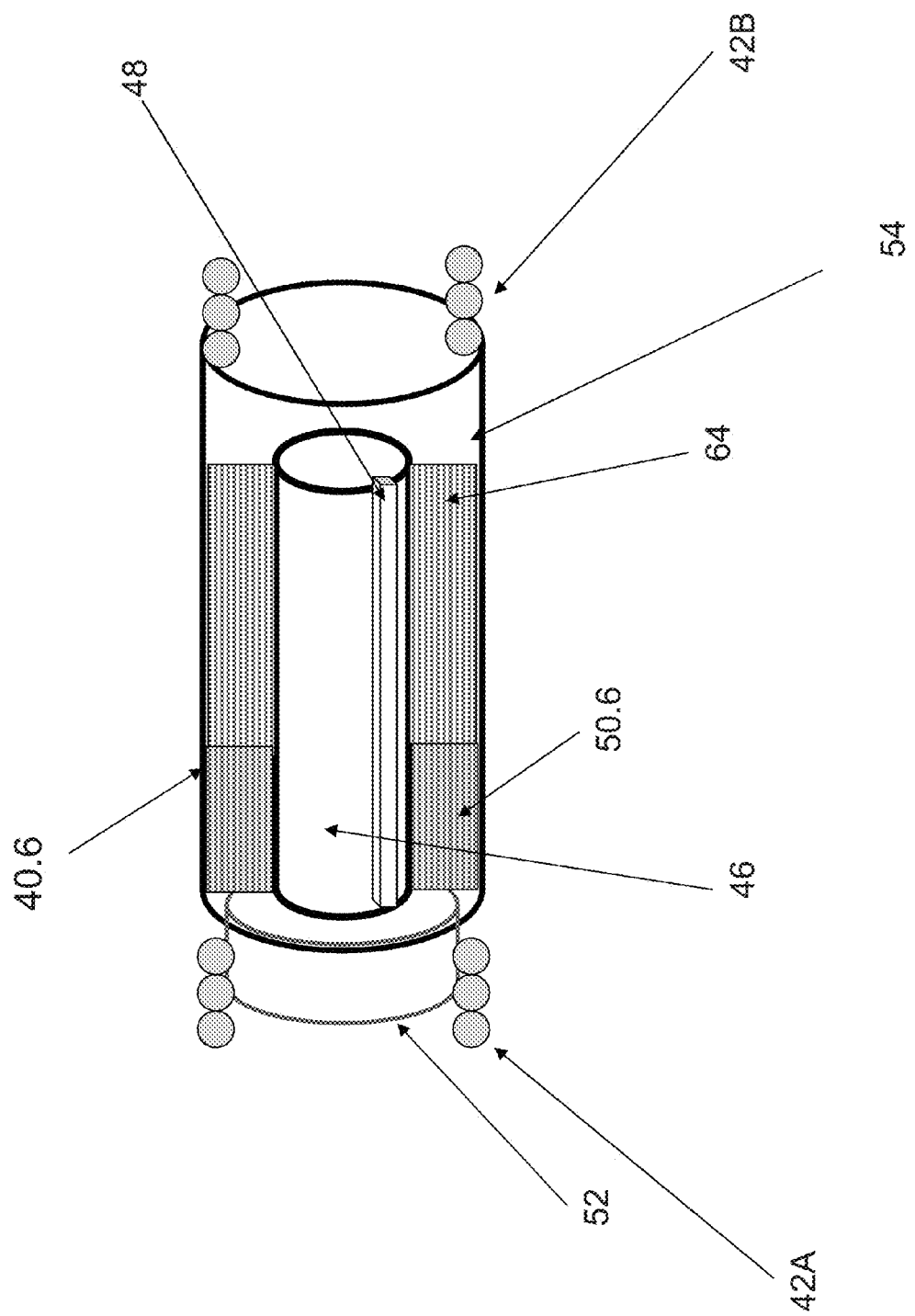
FIG. 7 shows a sixth embodiment of a sub-component according to the invention of an implantable device.
Figure 8:
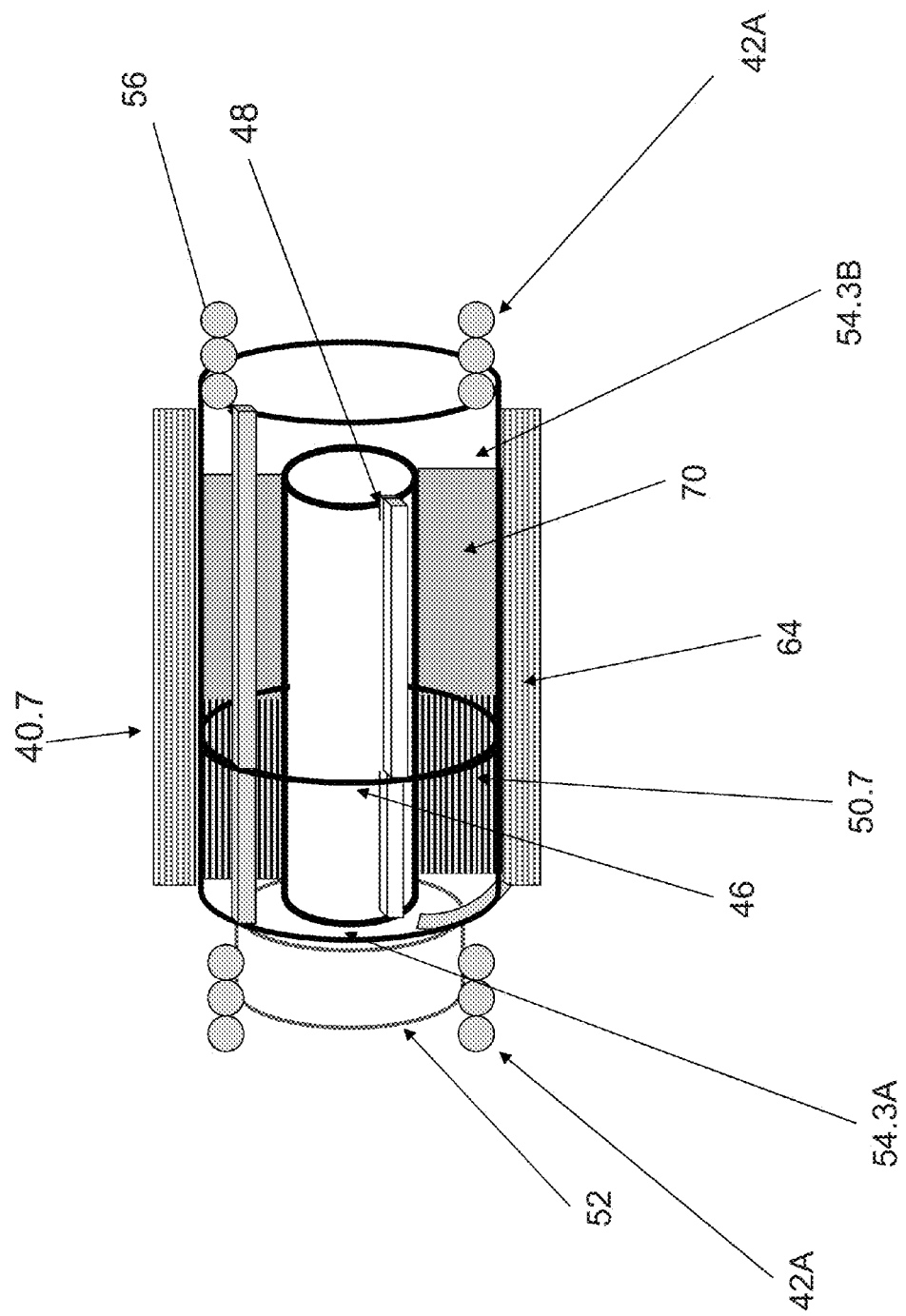
FIG. 8 shows a seventh embodiment of a sub-component according to the invention of an implantable device.

At least one embodiment of the invention, as shown in FIG. 5, may include a stop sleeve 52 that contacts a proximal portion 42A of the wire coil 42, as described above, and an outer sleeve 54.4, which may be slitted.

As shown in FIG. 5, by way of one or more embodiments, a wire 44 may be wound in a coiled manner as the inductive component, and the capacitive component of the sub-component 40.4 is produced from the parasitic capacitances between the wire windings of the wire 44. In at least one embodiment, the wire 44 may be wound on the slitted outer sleeve 54.4. In one or more embodiments, the wire 44 may also be wound on a slitted inner sleeve 46, as shown in FIG. 5. Alternatively to or in addition to the first coil 44 formed by the wire 44, at least one embodiment may include a second coil formed by wound wire 58 and having a winding direction opposite that of the first coil. In at least one embodiment, the second coil 58 may be arranged above the first coil 44, but may also equally be arranged below the first coil. In one or more embodiments, whilst the first coil formed by the wire 44 is electrically connected permanently to the wire coil 42, the second coil formed by the wire 58 may be connected via a magneto-resistive coupling element 60 to the wire coil 42. In at least one embodiment, the second coil formed by the wire 58 may only be effective when the magneto-resistive coupling element 60 is electrically conductive, for example in the presence of suitably high magnetic fields. As such, in one or more embodiments, the magneto-resistive coupling element 60, which forms the magneto-resistive component of the sub-component 40.4, is electrically conductive and the second coil formed by the wire 58 is effective. Due to the opposed direction of development of the second coil, by way of at least one embodiment, the magnetic fields of the first coil formed by the wire 44 and of the second coil formed by the wire 58 may cancel one another out at least approximately when the magneto-resistive coupling element 60 is conductive under the influence of a suitable strong magnetic field, such that the total inductance of the sub-component 40.4 decreases.

At least one embodiment of the invention, as shown in FIG. 5, may include a dielectric layer 62 as a dielectric between the slitted inner sleeve 46 and the slitted outer sleeve 54.4, such that the slitted inner sleeve 46 and the slitted outer sleeve 54.4 may form a capacitance and may include a further capacitive component of the sub-component 40.4.

Figure 9:
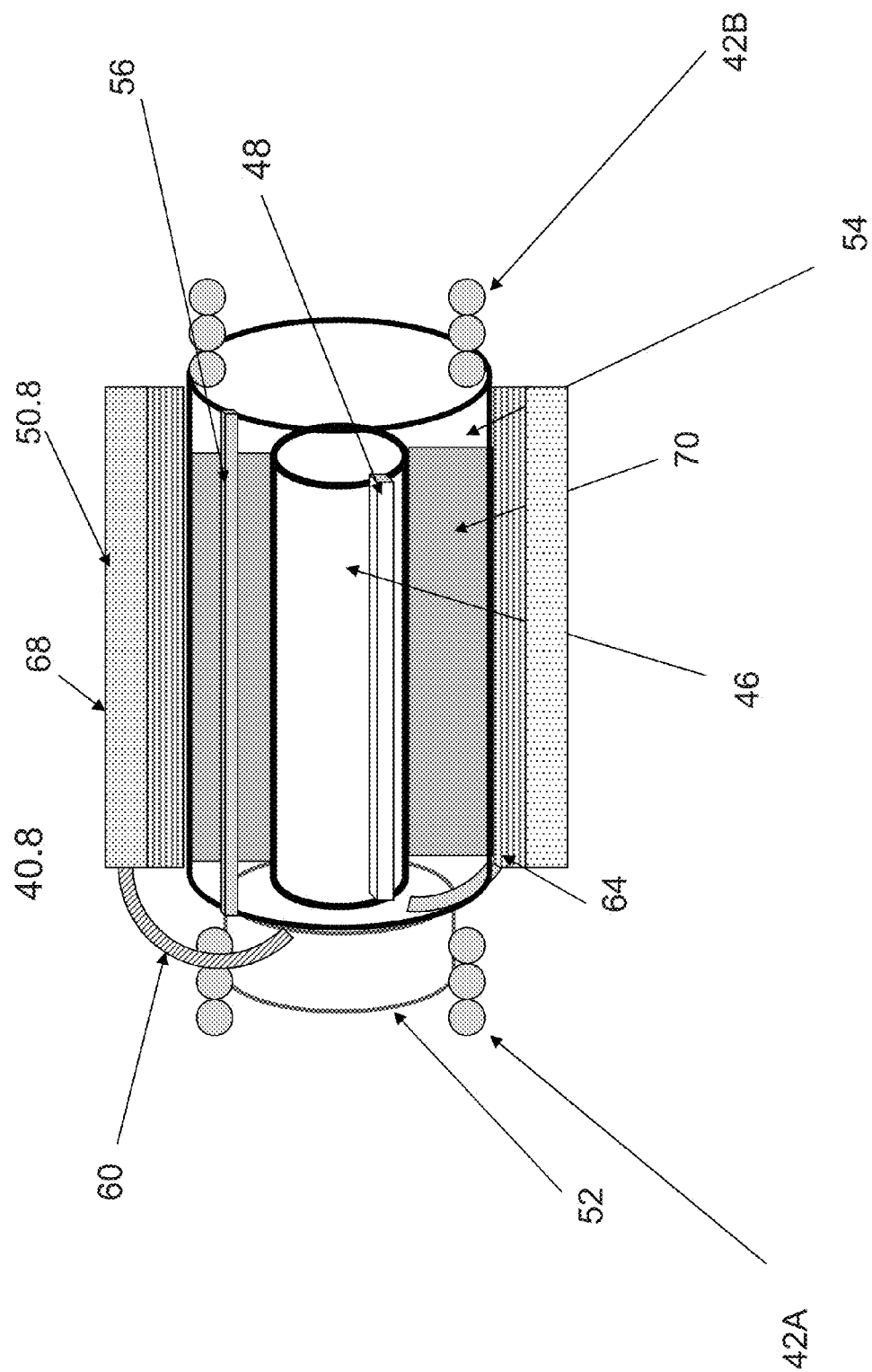
FIG. 9 shows an eighth embodiment of a sub-component according to the invention of an implantable device; and, FIG. 10 shows a magneto-resistive component that includes alternating layers of ferromagnetic and non-magnetic material.
Figure 10:
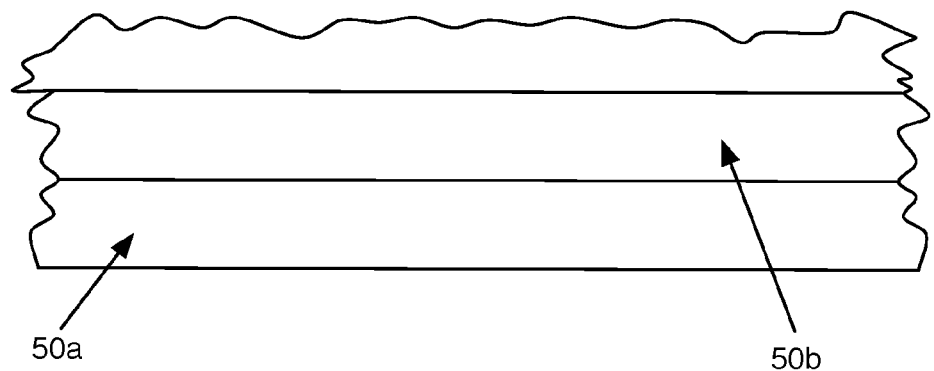

In one or more embodiments, the sub-components 40.5, 40.6, 40.7 and 40.8, as shown in FIGS. 6 to 9, differ from the sub-components shown in FIGS. 2 to 5 in that, in the subcomponents shown in FIGS. 6 to 9, the inductive component may be formed in each case by a spirally wound metalized film 64. In one or more embodiments, as shown in FIG. 9, which corresponds to the sub-component of FIG. 5, the film 68 may form the inductive component. Depending on the sub-component, the metalized film 64, such as of the wire 44, may be coated with magneto-resistive material 50.8. In at least one embodiment, the magneto-resistive materials 50 are denoted in FIGS. 6 to 9 by 50.5, 50.6, 50.7 and 50.8. As shown in FIG. 10, the at least one magneto-resistive component may include alternating layers of ferromagnetic material 50a and non-magnetic material 50b.

According to one or more embodiments of the invention, the sub-component 40 may be placed at an arbitrary or any point along the inner conductor 26 of an electrode line 20.

In at least one embodiment, the respective sub-component 40 may be placed at an arbitrary or any point along the outer conductor of an electrode line 20.

In one or more embodiments, the electrical conductors 26 may be formed as cables, wherein the sub-component 40 may be placed at an arbitrary or any point along the outer conductor of an electrode line 20.

According to at least one embodiment, the magneto-resistive effects may be anisotropic, for example dependent on the orientation in the magnetic field, wherein the magneto-resistive component may be formed geometrically. As such, the magneto-resistive component may still react isotropically, or at least sufficiently in each field orientation. For example, in one or more embodiments, three orthogonally oriented elements may be connected electrically in parallel. In at least one embodiment, as shown in FIGS. 3 to 5, the field sensitivity is already the same in two directions due to the rotational symmetry, and an isotropy may be produced by defined selection of the axial extension of the magneto-resistive element.

One or more embodiments of the invention may include self-adjustment of the filter formed by the sub-component, which may also be made for more than two magnetic field strengths, for example for the three strengths 1.5, 3 and 7 T by the use of a plurality of elements that are effective at different field strengths.

In at least one embodiment, the sub-component may be a filter which acts as a band-stop filter and which, at different Larmor frequencies, in particular for 1.5 T and 3 T devices, includes an effect >1 kOhm. In one or more embodiments, the resonance frequency of the band-stop filter may shift in accordance with the amplitude of the magnetic field in such a way that the stop frequency matches the Larmor frequency in each case.

According to one or more embodiments, the sub-component 40 connected in series, as discussed above, may include one or more of the following properties:

the magneto-resistive component includes a giant magnetoresistance (GMR) effect,
the magneto-resistive component includes an anisotropic magnetoresistance (AMR) effect,
the magneto-resistive component includes a colossal magnetoresistance (CMR) effect,
the magneto-resistive component includes a tunnel magnetoresistance (TMR) effect,
the magneto-resistive component includes alternating layers of ferromagnetic and non-magnetic material,
the magneto-resistive component is printed onto a substrate
the inductive component includes a wire wound in a coiled manner on a slitted metal sleeve,
the inductive component includes a metalized film wound in a spiraled manner on a slitted metal sleeve,
the capacitive component includes a slitted double sleeve,
a reduction of the resistivity of the magneto-resistive component leads to a reduced inductance of the indicative component,
a reduction of the resistivity of the magneto-resistive component leads to a reduced capacitance of the capacitive component,
a reduction of the resistivity of the magneto-resistive component leads both to a reduced capacitance of the capacitive component and to a reduced inductance of the inductive component,
a reduction of the resistivity of the magneto-resistive component leads to an at least partial short circuit of the inductive component,
a reduction of the resistivity of the magneto-resistive component leads to an at least partial short circuit of the capacitive component,
a reduction of the resistivity of the magneto-resistive component leads to an inductance that counteracts the inductance of the inductive component, and
a reduction of the resistivity of the magneto-resistive component leads to a transformation of the inductance of the inductive component toward a reduced inductance.

As a result of the sub-component according to at least one embodiment of the invention, a band-stop filter may be produced, of which the range of efficacy is expanded over a large frequency range without the need for fundamental modifications of the design of the filter. As such, in embodiments of the invention, no additional explicit parts are necessary.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS 10 heart stimulator
12 housing
14 terminal housing
16 electrical contacts
20 electrode line
22 electrode pole/point or tip electrode
24 electrode pole/ring electrode
26 electrical conductor/inner conductor
28 plug/plug contact
30 electrode pole
32 electrode pole
40 sub-component 42 wire coil
42A proximal portion
42B distal portion
44 wire/coil wound in a coiled manner
46 metal sleeve/inner sleeve
48 longitudinal slit
50 magneto-resistive component/material
52 stop sleeve
54 outer sleeve
56 slit
58 wire/second coil
60 magneto-resistive coupling element
62 dielectric layer
64 metalized film
68 film
70 dielectric

What is claimed is:

1. An implantable device comprising:
a proximal and a distal end;
at least one elongate electrically conductive component arranged between the proximal and the distal end; and,
a contact pole arranged in a region of the distal end configured to electrically contact bodily tissue adjacent to the contact pole during operation of the implantable device,
wherein the contact pole is electrically connected to the at least one elongate electrically conductive component,
wherein the at least one elongate electrically conductive component comprises a sub-component connected in series with a remainder of the at least one elongate electrically conductive component, and
wherein the sub-component comprises a capacitance, at least one inductive component and at least one magneto-resistive component which are arranged and configured in such a way that a reduction of a resistivity of the at least one magneto-resistive component leads to a shift of a resonance frequency of the sub-component.

2. The implantable device as claimed in claim 1, wherein the at least one magneto-resistive component comprises a material with an electrical resistance that decreases under an influence of a magnetic field.

3. The implantable device as claimed in claim 1, wherein the at least one magneto-resistive component is arranged such that the at least one magneto-resistive component at least partially bridges a slit between electrically conductive elements of the sub-component or a slit in an electrically conductive element of the sub-component.

4. The implantable device as claimed in claim 1, wherein the at least one magneto-resistive component comprises a material comprising at least one or more properties of a giant magnetoresistance (GMR) effect, an anisotropic magnetoresistance (AMR) effect, a colossal magnetoresistance (CMR) effect and a tunnel magnetoresistance (TMR) effect.

5. The implantable device as claimed in claim 1, wherein the at least one magneto-resistive component comprises alternating layers of ferromagnetic and non-magnetic material.

6. The implantable device as claimed in claim 1, wherein the at least one magneto-resistive component is printed onto a substrate.

7. The implantable device as claimed in claim 1, wherein the at least one inductive component comprises one or more of a wire wound in a coiled manner on a slitted metal sleeve and a metalized film wound in a spiraled manner on a slitted metal sleeve.

8. The implantable device as claimed in claim 1, wherein the at least one capacitive component comprises a slitted double sleeve.

9. The implantable device as claimed in claim 1, wherein the at least one capacitive component, the at least one inductive component and the at least one magneto-resistive component of the sub-component are arranged and connected such that a reduction of the resistivity of the at least one magneto-resistive component leads to a reduced inductance of the at least one inductive component.

10. The implantable device as claimed in claim 1, wherein the at least one capacitive component, the at least one inductive component and the at least one magneto-resistive component of the sub-component are arranged and connected such that a reduction of the resistivity of the at least one magneto-resistive component leads to a reduced capacitance of the at least one capacitive component.

11. The implantable device as claimed in claim 1, wherein the at least one capacitive component, the at least one inductive component and the at least one magneto-resistive component of the sub-component are arranged and connected such that a reduction of the resistivity of the at least one magneto-resistive component leads both to a reduced capacitance of the at least one capacitive component and to a reduced inductance of the at least one inductive component.

12. The implantable device as claimed in claim 1, wherein the at least one capacitive component, the at least one inductive component and the at least one magneto-resistive component of the sub-component are arranged and connected such that a reduction of the resistivity of the at least one magneto-resistive component leads to an at least partial short circuit of the at least one inductive component and to a change of an inductance of the at least one inductive component.

13. The implantable device as claimed in claim 1, wherein the at least one capacitive component, the at least one inductive component and the at least one magneto-resistive component of the sub-component are arranged and connected such that a reduction of the resistivity of the at least one magneto-resistive component leads to at least a partial short circuit of the at least one capacitive component and to a change of a capacitance of the at least one capacitive component.

14. The implantable device as claimed in claim 1, wherein the at least one capacitive component, the at least one inductive component and the at least one magneto-resistive component of the sub-component are arranged and connected such that a reduction of the resistivity of the at least one magneto-resistive component leads to a further inductance that counteracts an inductance of the at least one inductive component.

15. The implantable device as claimed in claim 1, wherein the at least one capacitive component, the at least one inductive component and the at least one magneto-resistive component of the sub-component are arranged and connected such that a reduction of the resistivity of the at least one magneto-resistive component leads to a transformation of an inductance of the at least one inductive component toward a reduced inductance.

* * * * *